(12) United States Patent
Park et al.

(10) Patent No.: US 7,682,814 B2
(45) Date of Patent: Mar. 23, 2010

(54) METHOD FOR PRODUCING LACTIC ACID WITH HIGH CONCENTRATION AND HIGH YIELD USING LACTIC ACID BACTERIA

(75) Inventors: Young Hoon Park, Seongnam-si (KR); Kwang Myung Cho, Icheon-si (KR); Hye Won Kim, Seongnam-si (KR); Dae Chol Kim, Suwon-si (KR)

(73) Assignee: CJ Cheiljedang Corp., Seoul (KR)

( * ) Notice: Subject to any disclaimer, the term of this patent is extended or adjusted under 35 U.S.C. 154(b) by 826 days.

(21) Appl. No.: 10/582,389

(22) PCT Filed: Nov. 18, 2004

(86) PCT No.: PCT/KR2004/002991

§ 371 (c)(1),
(2), (4) Date: Jun. 9, 2006

(87) PCT Pub. No.: WO2005/071061

PCT Pub. Date: Aug. 4, 2005

(65) Prior Publication Data

US 2007/0117193 A1    May 24, 2007

(30) Foreign Application Priority Data

Dec. 11, 2003  (KR) ................ 10-2003-0090204

(51) Int. Cl.
*C12N 1/00* (2006.01)
*C12N 1/20* (2006.01)

(52) U.S. Cl. .................. 435/243; 435/252.9

(58) Field of Classification Search ............. None
See application file for complete search history.

(56) References Cited

U.S. PATENT DOCUMENTS 6,475,759 B1 *  11/2002  Carlson et al. ............. 435/139

FOREIGN PATENT DOCUMENTS

| EP | 0861905 A2 | 9/1998 |
| WO | WO-97/04755 A1 | 2/1997 |
| WO | WO-97/09448 A1 | 3/1997 |
| WO | WO-99/29833 A1 | 6/1999 |
| WO | WO-99/62348 A1 | 12/1999 |
| WO | WO-02/18542 A1 | 3/2002 |

OTHER PUBLICATIONS

Richter et al., Acta Biotechnol. 1994, vol. 14, No. 4, p. 367-378.*
Alm L., J Dairy Sci, 1982, vol. 65, p. 515-520.*

* cited by examiner

*Primary Examiner*—L Blaine Lankford
*Assistant Examiner*—Kade Ariani
(74) *Attorney, Agent, or Firm*—Birch, Stewart, Kolasch & Birch, LLP

(57) ABSTRACT

The present invention relates to a method for producing lactic acid with high concentration and high yield using *Lactobacillus paracasei* CJLA0310 KCCM-10542 that is separated and identified from Kimchi. Lactic acid is a very important organic acid with a wide range of applications including food additive such as food preservative, condiment or acidifier, and industrial fields such as cosmetics, chemistry, metals, electronics, fabrics, dyeing textiles, and pharmaceutical industries. Particularly, lactic acid is an essential ingredient of polylactic acid, one of biodegradable plastics to replace recalcitrant non-biodegradable plastics which are main causes of environmental contamination.

4 Claims, 2 Drawing Sheets

METHOD FOR PRODUCING LACTIC ACID WITH HIGH CONCENTRATION AND HIGH YIELD USING LACTIC ACID BACTERIA

TECHNICAL FIELD

The present invention relates to a method for producing lactic acid using novel lactic acid bacteria. More particularly, the present invention relates to a method for producing lactic acid with high concentration and high yield using *Lactobacillus paracasei* CJLA0310 KCCM-10542 that is separated and identified from Kimchi.

BACKGROUND ART

Lactic acid is a very important organic acid and its applications are broad including food additive such as food preservative, condiment or acidifier, and industrial fields such as cosmetics, chemistry, metals, electronics, fabrics, dyeing textiles, and pharmaceutical industries. In addition, lactic acid is an essential ingredient of polylactic acid, one of biodegradable plastics. In recent years, there have been several concerns such as gas price increase, oil depletion and non-degradable petro-chemical based plastics. These concerns turn people's interests to environmentally-friendly polymer materials against recalcitrant non-biodegradable plastics which are main causes of environmental contamination. Accordingly, demand for lactic acid has been increased markedly. Worldwide production of lactic acid is approximately 100,000 tons every year, posting about 5% of growth. Considering the gradual increase in the biodegradable plastics, the demand for lactic acid will rise even higher within several years. Particularly, lactic acid is a very reactive organic acid containing a hydroxyl group and a carboxylic group. It is also used as a key ingredient of many chemicals including polylactic acid, acetaldehyde, polypropylene glycol, acrylic acid, and 2,3-pentathione. Moreover, lactic acid is used for preparation of ethyl lactate that is a biodegradable and non-toxic solvent widely used in manufacture of electronic instruments, paints or fabrics, detergents, adhesives or printings.

As described above, lactic acid is a very useful and valuable industrial material. Typically, lactic acid was produced through the traditional chemical synthesis or the biological fermentation process using carbohydrates as a substrate. The latter is preferred in many cases because the chemical synthesis creates other problems in addition to the material cost increase caused by the gas price increase or environmental contamination problems. For example, the traditional chemical synthesis of lactic acid not only produces lactic acid but also an inactive D, L lactic acid in form of a racemic mixture that consists of equal amount of D-lactic acid and L-lactic acid. Unfortunately though, the composition ratio of the D-lactic acid and the L-lactic acid cannot be controlled. Therefore, when the racemic lactic acid is used for preparing polylactic acid an amorphous polymer with low fusing point is produced, which in turn becomes an obstacle to the broad range of applications. On the other hand, the biological fermentation process using microorganisms makes it possible to selectively produce D-lactic acid or L-lactic acid depending on the strain used. For example, microorganisms such as *Lactobacillus*, *Bacillus*, *Rhizopus*, *Streptococcus*, and *Enterococcus* usually produce L-lactic acid. Microorganisms such as *Leuconostoc* and *Lactobacillus vulgaricus* usually produce D-lactic acid. The L-lactic acid is preferably used in cosmetic or food industries because the D-lactic acid is not metabolized in the body. Pure L-lactic acid can be used for the preparation of polylactic acid. In doing so, the polylactic acid is transformed into a crystal form having 180° C. of fusion point. Also, physical properties of the polylactic acid can be controlled by adjusting the content of the D-lactic acid for the polymerization. Overall, the L-lactic acid is applicable in replacement of various kinds of plastics.

As described above, lactic acid has a great potential to be an environmentally-friendly replacement material in a wide range of industrial applications. Thus, it is very important to develop a method for producing lactic acid through the biological fermentation which is more economical than the traditional chemical synthesis. To this end, there is an urgent need to develop a lactic acid-producing strain and a cost-effective method for producing lactic acid.

DESCRIPTION OF THE DRAWINGS

The above and other objects, features and other advantages of the present invention will be more clearly understood from the following detailed description taken in conjunction with the accompanying drawings, in which.

DISCLOSURE

Technical Problem

Figure 1:
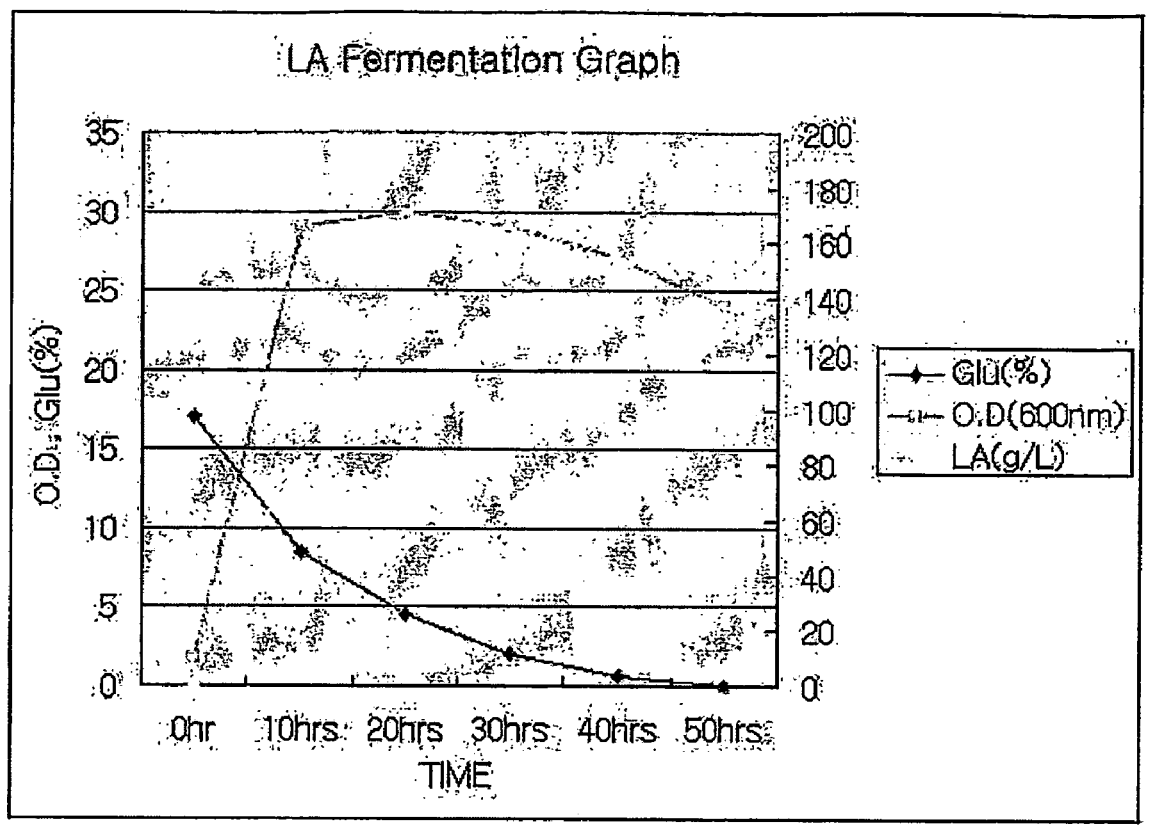
FIG. 1 is a graph showing the relation between fermentation time and cell concentration, glucose concentration and lactic acid concentration in lactic acid fermentation using *Lactobacillus paracasei* CJLA0310 in a culture medium consisting of 180 g/L of glucose, 15 g/L of yeast extract, and 10 g/L of peptone.

Therefore, the present invention has been made in view of the above problems, and it is an object of the present invention to provide a lactic acid-producing microorganism to produce industrially useful lactic acid more effectively through biological fermentation. More specifically, the present invention is directed to develop a method for producing industrially useful lactic acid bacteria with high concentration and high yield, the method involving the separation of lactic acid bacteria characterized of excellent growth efficiency and lactic acid production capacity.

It is another object of the present invention to provide a lactic acid producing strain that features high lactic acid yield during the biological lactic acid fermentation process, high lactic acid concentration in a fermentation broth at the end of the fermentation process, short fermentation time, high productivity and high economic efficiency.

Technical Solution

In accordance with an aspect of the present invention, the above and other objects can be accomplished by the provision of a method for producing high-purity lactic acid using novel lactic acid bacteria separated and identified as *Lactobacillus paracasei* CJLA0310 KCCM-10542 featuring excellent lactic acid production capacity.

In accordance with another aspect of the present invention, there is provided a fermentation method for producing lactic acid with high concentration and high yield using a *Lactobacillus paracasei* CJLA0310 strain that is separated and identified from Kimchi, and a method for adjusting a production ratio of L-lactic acid and D-lactic acid under proper culture conditions using the strain.

In accordance with another aspect of the present invention, there is suggested the possibility of reducing production cost of lactic acid by utilizing low-price corn steep powder in replacement of yeast extract in a medium, which is known as a key factor for increasing the cost of manufacture.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

ADVANTAGEOUS EFFECTS

*Lactobacillus paracasei* CJLA0310 is a lactic acid-producing strain separated from Kimchi, and under proper culture conditions it can produce an optically pure L-lactic acid with high concentration and high yield. The present invention provides biological production of the L-lactic acid which is one of industrially useful organic acids. Because the biological production makes it possible to mass-produce lactic acid with high yield and high productivity with respect to carbohydrates, the present invention can be very advantageously used for the food and environment industries.

MODE FOR CARRYING OUT THE INVENTION

Example 1

Separation and Identification of Lactic Acid Producing Bacteria

The present inventors separated the fluid of Kimchi that was collected from a waste Kimchi disposal unit in Icheon 1 Kimchi factory of CJ CORP. located in Icheon-si, Gyeonggi-do, Korea. The fluid was then diluted with physiological saline solution (8.5 g/L NaCl) and smeared uniformly over the MRS medium (manufactured by Difco Co.). After two days of cultivation at 37° C., colonies were separated and particularly yellowish colonies among them were assumed to be lactic acid bacterium. 12 largest colonies out of the yellowish colonies were separated and cultivated, respectively, in the MRS liquid mediums at 37° C. for two days, in order to obtain a strain of the highest cell growth rate and lactic acid production capacity. Part of base sequence (800 bp) of 16S rDNA of the strain was compared with DNA base sequence database of 11 kinds of *Lactobacillus* standard strains. As shown in Table 1 below, it was observed that the DNA base sequence of the separated strain manifested 89% of similarity to that of the *Lactobacillus* standard strain. Especially, the strain turned out to be a novel *Lactobacillus* microorganism exhibiting 100% of similarity to *Lactobacillus paracasei* subsp. *paracasei* and *Lactobacillus paracasei* subsp. *tolerans*. Therefore, the strain was named *Lactobacillus paracasei* CJLA0310. The strain was deposited with the KCCM (Korean Culture Center of Microorganisms located at 361-221, Yurim B/D, Hongje-1-dong, Seodaemun-gu, Seoul 120-091, Republic of Korea) on Dec. 5, 2003 under the Budapest Treaty, and given the number KCCM-10542.

TABLE 1

16s rDNA base sequence similarity between CJLA0310 and *Lactobacillus* standard strain

| Strain name | Similarity (%) |
|---|---|
| *Lactobacillus paracasei* subsp. *Paracasei* JCM 8130T | 100.00 |
| *Lactobacillus paracasei* subsp. *tolerans* JCM 1171T | 100.00 |
| *Lactobacillus zeae* ATCC 15820T | 98.63 |
| *Lactobacillus casei* JCM 1134T | 98.62 |
| *Lactobacillus rhamnosus* JCM 1136T | 97.87 |
| *Lactobacillus vermiforme* ATCC 13133 | 91.06 |
| *Lactobacillus hilgardii* ATCC 8290T | 90.96 |
| *Lactobacillus collinoides* JCM 1123T | 90.72 |
| *Lactobacillus paraplantarum* DSM 10667T | 89.99 |
| *Lactobacillus pentosus* JCM 1558T | 89.86 |
| *Lactobacillus plantarum* JCM 1149T | 89.86 |

Example 2

Lactic Acid Fermentation Characteristics of Novel Microorganism (180 g/L of Glucose+15 g/L of Yeast Extract+10 g/L of Peptone)

Figure 2:
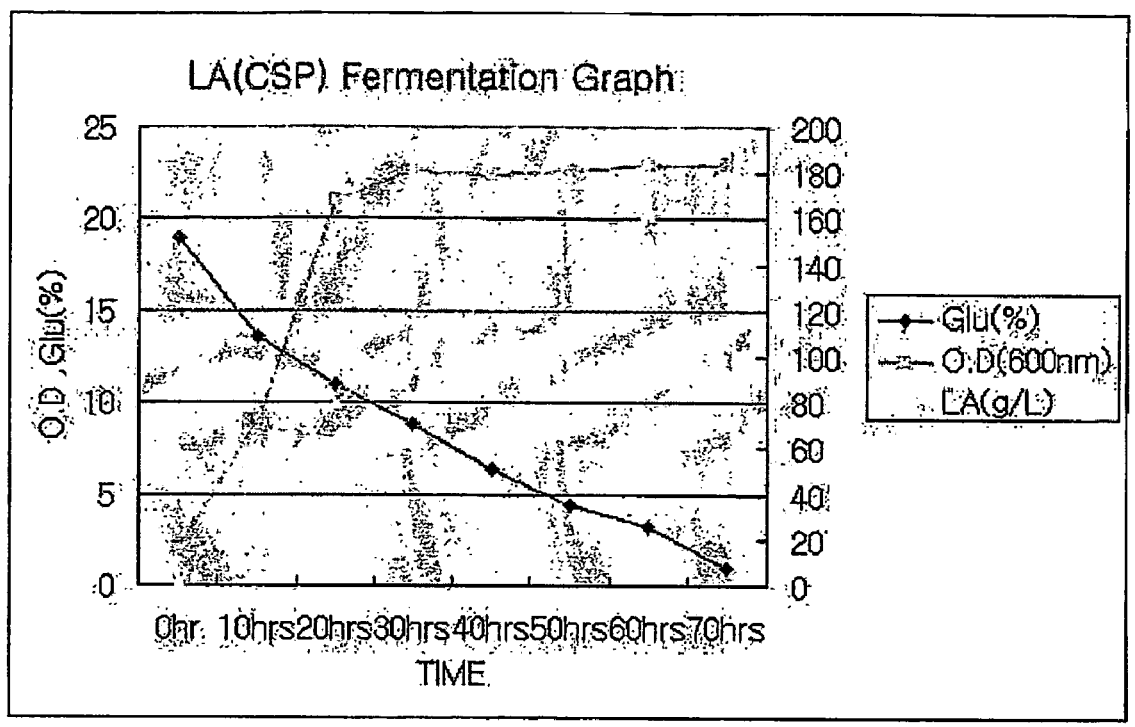
FIG. 2 is a graph showing the relation between fermentation time and cell concentration, glucose concentration and lactic acid concentration in lactic acid fermentation using *Lactobacillus paracasei* CJLA0310 in a culture medium consisting of 180 g/L of glucose, 7 g/L of peptone, and 15 g/L of CSP(Corn Steep Powder).

To cultivate the novel lactic acid CJLA0310, 600 ml of inoculum was first seeded for 18 hours in a medium consisting of 180 g/L of glucose, 15 g/L of yeast extract, and 10 g/L of peptone. Then, the inoculum was seeded in a fermenter (5 L) containing 2.4 L of the fermentation medium which consisted of 180 g/L of glucose, 15 g/L of yeast extract, and 10 g/L of peptone. The inoculum was cultured for 50 hours at pH 6.0, 200 rpm, and 37° C. As shown in FIG. 2, after 50 hours of the cultivation process 180 g of glucose was consumed, the cell growth medium (O.D.$_{600}$)=24, and 181 g/L of lactic acid was finally produced. Therefore, the lactic acid yield=99.5%, and average volume productivity per hour=3.85 g/L/hr.

Example 3

Lactic Acid Fermentation Characteristics of Novel Microorganism (160 g/L of Glucose+15 g/fL of Yeast Extract+15 g/L of Peptone)

To cultivate the novel lactic acid CJLA0310, 600 ml of inoculum was first seeded for 18 hours in the medium of Example 2. Then, the inoculum was seeded in a fermenter (5 L) containing 2.4 L of the fermentation medium which consisted of 160 g/L of glucose, 15 g/L of yeast extract, and 15 g/L of peptone. The inoculum was cultured for 50 hours at pH 6.0, 200 rpm, and 33, 35, 37, 39 and 41° C., respectively. As shown in Table. 2, the fermentation ratio of D-lactic acid and L-lactic acid could be adjusted according to the fermentation temperatures.

TABLE 2

Relation between production ratio of D-lactic acid and L-lactic acid and fermentation temperatures

| | Fermentation Temperature (° C.) | | | | |
|---|---|---|---|---|---|
| | 33 | 35 | 37 | 39 | 41 |
| Fermentation ratio (%) (D-lactic acid:L-lactic acid) | 4.0:96.0 | 3.5:96.5 | 3.3:96.7 | 3.1:96.9 | 0.7:99.3 |

Example 4

Lactic Acid Fermentation Characteristics of Novel Microorganism (180 g/L of Glucose+7 g/L of Peptone+15 g/L of CSP)

To cultivate the novel lactic acid CJLA0310, 600 ml of inoculum was first seeded for 18 hours in the medium of Example 2. Then, the inoculum was seeded in a fermenter (5 L) containing 2.4 L of the fermentation medium which consisted of 180 g/L of glucose, 7 g/L of peptone and 15 g/L of CSP (corn steep powder). The inoculum was cultured for 70 hours at pH 6.0, 200 rpm, and 37° C. As shown in FIG. 2, after 65 hours of the cultivation process 180 g of glucose was consumed, the cell growth medium (O.D.$_{600}$)=24, and 179.1 g/L of lactic acid was finally produced. Therefore, the lactic acid yield=99.5%, and average volume productivity per hour=2.76 g/L/hr.

The invention claimed is:

1. An isolated *Lactobacillus paracasei* CJLA0310 (Accession Number: KCCM-10542) strain from Kimchi, characterized by having excellent lactic acid production capacity and high growth rate.

2. A method for producing lactic acid with high concentration by cultivating the strain of claim 1 in a medium that comprises 160-180 g/L of glucose, 15 g/L of yeast extract, and 7-15 g/L of peptone.

3. The method according to claim 2, wherein the production ratio of D-lactic acid and L-lactic acid is adjusted by varying the cultivation temperature in a range of 33-41° C.

4. The method according to claim 2, wherein the medium comprises corn steep powder in replacement of yeast extract.

* * * * *